United States Patent
Yamanouchi et al.

(10) Patent No.: US 11,298,504 B2
(45) Date of Patent: Apr. 12, 2022

(54) MEDICAL DEVICE

(71) Applicants: KAWASUMI LABORATORIES, INC., Saiki (JP); Dai Yamanouchi, Verona, WI (US)

(72) Inventors: Dai Yamanouchi, Verona, WI (US); Akira Bonkohara, Bungo-Ono (JP)

(73) Assignees: KAWASUMI LABORATORIES, INC., Saiki (JP); Dai Yamanouchi, Verona, WI (US)

( * ) Notice: Subject to any disclaimer, the term of this patent is extended or adjusted under 35 U.S.C. 154(b) by 92 days.

(21) Appl. No.: 16/005,893

(22) Filed: Jun. 12, 2018

(65) Prior Publication Data

US 2018/0353727 A1 Dec. 13, 2018

(30) Foreign Application Priority Data

Jun. 13, 2017 (JP) .............................. JP2017-116193

(51) Int. Cl.
*A61M 25/00* (2006.01)
*A61B 17/221* (2006.01)
(Continued)

(52) U.S. Cl.
CPC ......... *A61M 25/0023* (2013.01); *A61B 17/22* (2013.01); *A61B 17/221* (2013.01);
(Continued)

(58) Field of Classification Search
CPC .......... A61M 25/0082; A61M 25/0068; A61M 25/003; A61M 2025/0096;
(Continued)

(56) References Cited

U.S. PATENT DOCUMENTS 5,011,488 A * 4/1991 Ginsburg ............... A61B 17/22
604/104
5,908,435 A * 6/1999 Samuels .......... A61B 17/22031
606/127

(Continued)

FOREIGN PATENT DOCUMENTS

JP 2007-252895 A 10/2007
JP 2008-23318 A 2/2008
(Continued)

OTHER PUBLICATIONS

Office Action dated Apr. 6, 2021, issued by the Japan Patent Office in counterpart Japanese Patent Machine Application No. 2017-116193.

*Primary Examiner* — Amber R Stiles
(74) *Attorney, Agent, or Firm* — Sughrue Mion, PLLC

(57) ABSTRACT

A medical device is configured to treat a body cavity. The medical device includes a tubular sheath portion, a foreign substance capturing catheter configured to be movable inside the sheath portion, the foreign substance capturing catheter having a capturing portion configured to capture a foreign substance inside the body cavity, a treatment catheter configured to be movable inside the foreign substance capturing catheter, the treatment catheter having a treatment portion configured to treat the body cavity. The medical device is configured to be inserted into the body cavity in a state in which the treatment catheter is set inside the foreign substance capturing catheter and the foreign substance capturing catheter is set inside the sheath portion.

7 Claims, 3 Drawing Sheets

(51) Int. Cl.
*A61B 17/22* (2006.01)
*A61M 25/09* (2006.01)
*A61B 17/00* (2006.01)
*A61M 25/06* (2006.01)

(52) U.S. Cl.
CPC .... *A61M 25/0068* (2013.01); *A61M 25/0082* (2013.01); *A61B 2017/00867* (2013.01); *A61B 2017/2212* (2013.01); *A61B 2017/22082* (2013.01); *A61M 25/09* (2013.01); *A61M 2025/0024* (2013.01); *A61M 2025/0096* (2013.01); *A61M 2025/0681* (2013.01)

(58) Field of Classification Search
CPC .. A61M 2025/0024; A61M 2025/0681; A61M 25/0023; A61M 25/09; A61B 17/22; A61B 17/221; A61B 2017/2212; A61B 2017/22081; A61B 2017/22082; A61B 2017/00831; A61B 2017/00867
See application file for complete search history.

(56) References Cited

U.S. PATENT DOCUMENTS

| | | | | |
|---|---|---|---|---|
| 6,221,006 | B1* | 4/2001 | Dubrul | A61B 17/221 600/159 |
| 10,231,751 | B2* | 3/2019 | Sos | A61B 17/22032 |
| 2005/0038468 | A1* | 2/2005 | Panetta | A61F 2/013 606/200 |
| 2005/0070844 | A1* | 3/2005 | Chow | A61M 25/0054 604/95.04 |
| 2005/0245894 | A1* | 11/2005 | Zadno-Azizi | A61B 17/12045 604/509 |
| 2007/0197962 | A1* | 8/2007 | Morikawa | A61M 25/1006 604/96.01 |
| 2007/0293887 | A1 | 12/2007 | Okushi et al. | |
| 2010/0016832 | A1* | 1/2010 | Thai | A61M 25/007 604/508 |
| 2010/0217276 | A1* | 8/2010 | Garrison | A61M 25/0662 606/128 |
| 2010/0292721 | A1 | 11/2010 | Moberg | |
| 2011/0251629 | A1 | 10/2011 | Galdonik et al. | |
| 2012/0059309 | A1* | 3/2012 | di Palma | A61M 25/007 604/22 |
| 2012/0215239 | A1 | 8/2012 | Moberg | |
| 2014/0088625 | A1 | 3/2014 | Moberg | |
| 2014/0371782 | A1 | 12/2014 | Galdonik et al. | |
| 2015/0150589 | A1* | 6/2015 | Yamanouchi | A61B 17/320758 606/159 |
| 2015/0313732 | A1* | 11/2015 | Fulton, III | A61B 17/22 623/1.11 |
| 2016/0166265 | A1* | 6/2016 | Nita | A61B 17/320758 606/127 |
| 2016/0367285 | A1* | 12/2016 | Sos | A61F 2/013 |
| 2017/0164964 | A1 | 6/2017 | Galdonik et al. | |
| 2019/0008550 | A1 | 1/2019 | Yamanouchi | |
| 2020/0046389 | A1 | 2/2020 | Galdonik et al. | |

FOREIGN PATENT DOCUMENTS

| | | |
|---|---|---|
| JP | 2012-526636 A | 11/2012 |
| JP | 2013-523404 A | 6/2013 |
| JP | 2015-107301 A | 6/2015 |
| WO | 2011/151911 A1 | 12/2011 |

* cited by examiner

US 11,298,504 B2

MEDICAL DEVICE

CROSS-REFERENCE TO RELATED APPLICATION

The present application claims priority from Japanese Patent Application No. 2017-116193 filed on Jun. 13, 2017, the entire content of which is incorporated herein by reference.

FIELD OF INVENTION

The present invention relates to a medical device.

RELATED ART

A related art catheter removes foreign substance such as a thrombus or an embolus generated in a blood vessel. The catheter includes an expansion part at a distal end of a body of the catheter (see, e.g., JP2007-252895A). With this catheter, the expansion part expands at downstream of a treatment site to prevent foreign substance peeled off from the treatment site from scattering.

When inserting the related art catheter percutaneously into a blood vessel, for example, there are following approaches: (A) an introducer sheath (a sheath and dilator assembly) is used and a foreign substance removing catheter having an collapsed expansion part is inserted into the introducer sheath; or (B) a introducer sheath is not used, a dilator is directly inserted into a lumen of a catheter body, and then a foreign substance removing catheter having a collapsed expansion part is inserted into a blood vessel.

However, with the approach (A), the dilator needs to be drawn out from the sheath after the introducer sheath is introduced into a blood vessel. Also with the approach (B), the dilator needs be removed from the catheter body after the foreign substance removing catheter is inserted into the blood vessel. That is, in either case, the dilator needs to be pulled out of the blood vessel with a long guide wire inserted and left in the blood vessel, which require complicated procedures.

SUMMARY

Illustrative aspects of the present invention provide a medical device capable of reducing a work burden on a user.

According to an illustrative aspect of the invention, a medical device is configured to treat a body cavity. The medical device includes a tubular sheath portion, a foreign substance capturing catheter configured to be movable inside the sheath portion, the foreign substance capturing catheter having a capturing portion configured to capture a foreign substance inside the body cavity, a treatment catheter configured to be movable inside the foreign substance capturing catheter, the treatment catheter having a treatment portion configured to treat the body cavity. The medical device is configured to be inserted into the body cavity in a state in which the treatment catheter is set inside the foreign substance capturing catheter and the foreign substance capturing catheter is set inside the sheath portion.

Other aspects and advantages of the invention will be apparent from the following description, the drawings and the claims.

DETAILED DESCRIPTION

Figure 1:
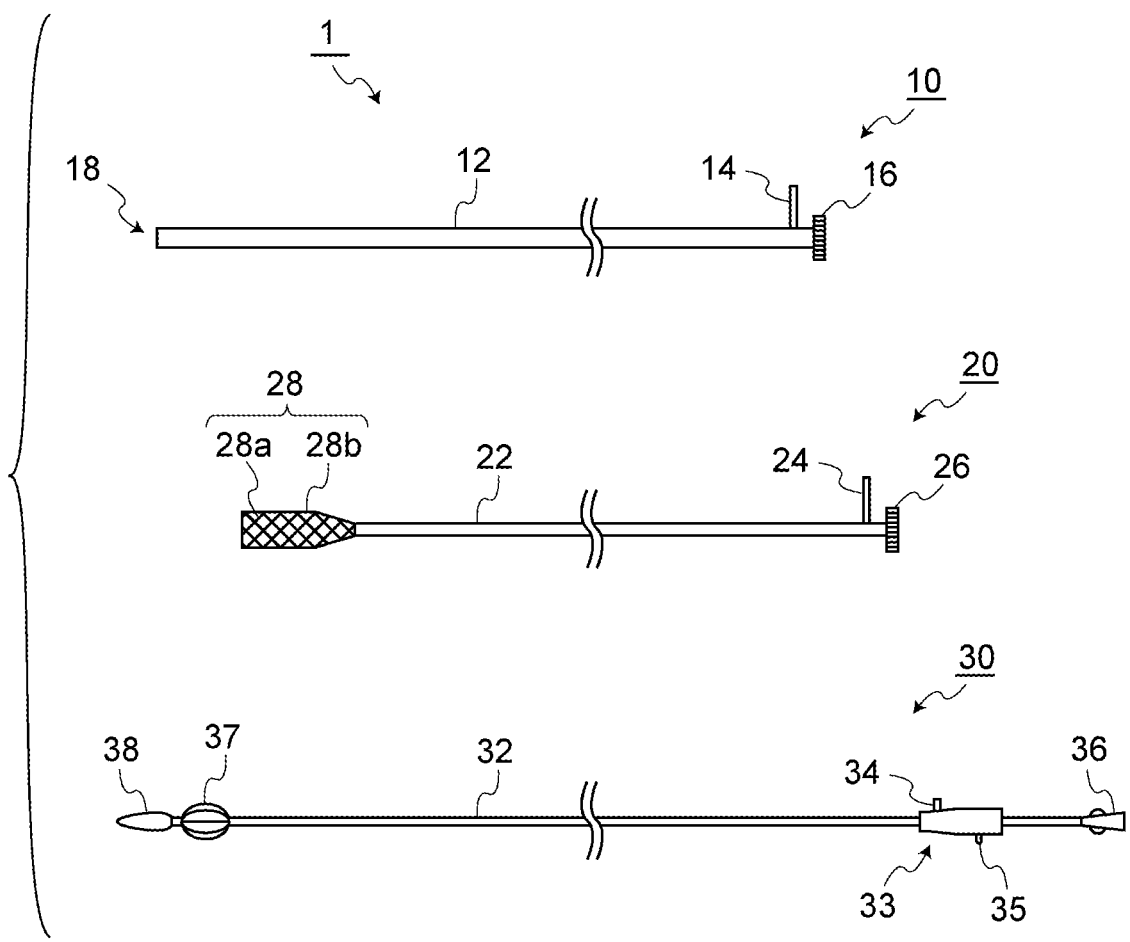
FIG. 1 illustrates an overall configuration of a medical device according to a first exemplary embodiment of the present invention.

Hereinafter, exemplary embodiments of the present invention will be described in detail with reference to the drawings.

First, a medical device 1 according to a first exemplary embodiment of the invention will be described with reference to FIGS. 1 and 2. For the purpose of facilitating the understanding of the present invention, in FIGS. 1 and 2, the lengths, thicknesses, wall thicknesses, and the like of components of the medical device 1 are shown in an exaggerated manner.

In the following description, the term "distal portion" or "distal end portion" refers to an end portion that is farther from a user of the medical device 1, and the term "proximal portion" or "base end portion" refers to an end portion closer to the user of the medical device 1.

The medical device 1 is configured to remove foreign substance, such as a thrombus or an embolus generated in a blood vessel. As illustrated in FIG. 1, the medical device 1 includes a tubular sheath portion 10, a foreign substance capturing catheter 20 configured to be movable inside the sheath portion 10, and a foreign substance removing catheter 30 configured to be movable inside the foreign substance capturing catheter 20.

The sheath portion 10 includes an elongated sheath tube 12, an injection port 14 provided at a proximal portion of the sheath tube 12, a first valve 16 provided at a proximal end of the sheath tube 12.

While not illustrated in the drawings, the sheath tube 12 has a lumen configured to allow the foreign substance capturing catheter 20 to pass through.

The sheath tube 12 is made of a flexible material, for example, a synthetic resin (elastomer), a resin compound which is a mixture of a synthetic resin and other materials, a multi-layered structure in which multiple layers of synthetic resin are stacked, or a composite of a synthetic resin and a metal wire.

The injection port 14 is in communication with the lumen of the sheath tube 12 and is configured such that the sheath tube 12 can be filled with a liquid, such as saline through the injection port 14. While not illustrated in the drawings, an opening of the injection port 14 is closed in a liquid-tight manner by using a closing member such as a cap or a valve made of a silicon rubber or the like.

A first valve 16, an example of a first anti-falling structure, is configured to prevent blood or the like from leaking from the sheath tube 12, and to prevent the foreign substance capturing catheter 20 inserted into the sheath portion 10 from being displaced or from falling apart.

The foreign substance capturing catheter 20 includes an elongated catheter tube 22, an injection port 24 provided at a proximal portion of the catheter tube 22, a second valve 26 provided at a proximal end of the catheter tube 22, and a capturing portion 28 provided at a distal end of the catheter tube 22. The foreign substance capturing catheter 20 is a thrombus capturing catheter for capturing foreign substance, such as a thrombus or an embolus generated in a blood vessel.

While not illustrated in the drawings, the catheter 22 has a lumen configured to allow the foreign substance removing catheter 30 to pass through the catheter tube 22. The outer diameter of the catheter tube 22 is equal to or smaller than the inner diameter of the sheath tube 12.

The material of the catheter tube 22 is the same as that of the sheath tube 12. Therefore, a detailed description thereof will be omitted.

The injection port 24 is in communication with the lumen of the catheter tube 22 and is configured such that a liquid such as saline, for example, is charged into in the catheter tube 22 via the injection port 24. While not illustrated in the drawings, an opening of the injection port 24 can be closed in a liquid-tight manner by a closing member such as a cap or a valve made of a silicon rubber or the like.

The second valve 26, an example of a second anti-falling structure, is configured to prevent blood or the like from leaking from the catheter tube 22 and to prevent the foreign substance removing catheter 30 inserted into the foreign substance capturing catheter 20 from being undesirably displaced or from falling apart.

The capturing portion 28 is configured to capture a foreign substance present in the blood vessel. The capturing portion 28 is formed with, for example, a cylindrical mesh portion 28a and a membrane portion 28b configured to surround the mesh portion 28a. The mesh portion 28a is formed by weaving metal wires of stainless steel, a Ni—Ti alloy, or a titanium alloy into a lattice shape, and is configured to be capable of expanding and contracting in the radial direction (direction orthogonal to the axial direction). Preferably, the membrane portion 28b may be made of, for example, fluoro-resin such as polytetrafluoroethylene (PTFE), polyurethane resin, etc. The membrane portion made of the resin material has good biocompatibility and durability and may be chemically stable.

The foreign substance removing catheter 30 serving as a treatment catheter includes an elongated catheter tube 32, an operation portion 33 disposed at a proximal portion of the catheter tube 32, and an injection port 34 and an operation lever 35 that are installed on a flank surface of the operation portion 33, a connector 36 provided at a proximal end of the catheter tube 32, a removing portion 37 provided at a distal portion of the catheter tube 32, and a distal end tip 38 provided at a distal end of the catheter tube 32. The foreign substance removing catheter 30 is a catheter for removing foreign substance such as a thrombus or an embolus generated in a blood vessel.

While not illustrated in the drawings, the catheter tube 32 has a lumen configured to allow a guide wire, drug solution, and the like to pass through. The operation portion 33, the removing portion 37, and the distal end tip 38 each has a similar lumen to allow a guide wire or drug solution, and the like to pass through. The outer diameter of the catheter tube 32 is equal to or smaller than the inner diameter of the catheter tube 22 (the foreign substance capturing catheter 20).

The operation portion 33 is a component that is operated by a user to expand or collapse the removing portion 37 by using the operation lever 35.

The injection port 34 is in communication with the lumen of the catheter tube 32 and is configured such that a liquid such as saline, for example, is charged into in the catheter tube 32 via the injection port 34. While not illustrated in the drawings, an opening of the injection port 34 can be closed in a liquid-tight manner by a closing member such as a cap or a valve made of a silicon rubber or the like.

The connector 36 is provided with a hemostatic valve (not illustrated), and such as a guide wire or the like may be inserted into the connector.

The removing portion 37 has, for example, a plurality of metal wires extending along the axial direction (the longitudinal direction of the foreign substance removing catheter 30). As illustrated in FIG. 1, the removing portion is configured to expand to a substantially spherical shape and to contract to a diameter substantially the same as that of the catheter tube 32.

As the material of the metal wires constituting the removing portion 37, for example, as well-known a metal or a metal alloy typified by stainless steel, a Ni—Ti alloy, a titanium alloy, or the like may be favorably used. The metal wires are made of a material having elasticity (reversible property of returning to its original shape when the force is removed when being in a deformed state). A Ni—Ti alloy may be suitably used as a material having super-elasticity. When the metal wires are made of an alloy with X-ray contrasting properties, the removing portion may be used as an X-ray impermeable marker. In this case, the user can visually monitor the position of the removing portion from outside of the body.

The distal end tip 38 is configured to be close an open end 18 of the sheath portion 10 in a state in which the foreign substance removing catheter 30 is set inside the foreign substance capturing catheter 20 and the foreign substance capturing catheter 20 is set inside the sheath portion 10. The distal end tip 38 is also configured to unclose the open end 18 of the sheath portion 10 when the foreign substance removing catheter 30 is moved in a distal direction relative to the sheath portion 10.

The overall shape of the distal end tip 38 is, for example, a substantially spherical shape (a shape resembling a rugby ball). The maximum diameter of the distal end tip 38 is approximately the same as the diameter of the sheath tube 12 for eliminating uneven steps from the sheath tube 12 when the open end 18 of the sheath tube 12.

As a material for the distal end tip 38, for example, various materials having appropriate rigidity and flexibility, such as a synthetic resin (or an elastomer thereof) including a polyamide-based resin, a polyurethane-based resin, a polyvinyl chloride-based resin, and the like can be preferably used.

Next, a method of using of the medical device 1 will be described.

Figure 2:
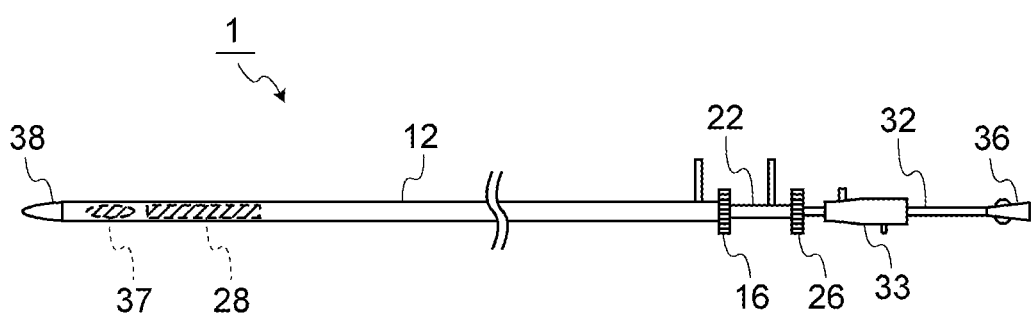
FIG. 2 illustrates a state in which components of the medical device of FIG. 1 are assembled.

As illustrated in FIG. 2, before the use of the medical device 1, the foreign substance removing catheter 30 is set inside the foreign substance capturing catheter 20 and the foreign substance capturing catheter 20 is set inside the sheath portion 10.

In a state in which the guide wire is first inserted in the blood vessel, the medical device 1 illustrated in FIG. 2 is inserted into the blood vessel to be aligned with the guide wire, and then the medical device 1 is further advanced to reach a position right in front of a target position (a region where a foreign substance is present).

Next, in a state in which a position of the sheath portion 10 is fixed, the foreign substance capturing catheter 20 and the foreign substance removing catheter 30 are moved forward such that the foreign substance capturing catheter 20 and the foreign substance removing catheter 30 advances and protrudes from the sheath portion 10. The sheath portion 10 may be moved backward with the foreign substance capturing catheter 20 and the foreign substance removing catheter 30 are fixed in place.

In a state in which the capturing portion 28 of the foreign substance capturing catheter 20 is expanded, foreign substance in the blood vessel is entangled with the removing portion 37 of the foreign substance removing catheter 30. For example, the removing portion 37 may be rotated around the tube axis at the target site, or may be reciprocated at the target site, or may be repeatedly inflated and deflated, so as to be intertwined with the foreign substance.

Then, with the foreign substance entangled with the removing portion 37, the removing portion 37 is contracted, and the removing portion 37 and the capturing portion 28 are withdrawn into the sheath portion 10. Thereafter, by extracting the foreign substance capturing catheter 20 and the foreign substance removing catheter 30 from the sheath portion 10, the foreign substance can be taken out of the body percutaneously. It is also possible to extract only the foreign substance removing catheter 30 from the foreign substance capturing catheter 20 while the foreign substance capturing catheter 20 remains in the sheath portion 10.

As described above, the medical device 1 is configured to be inserted into the blood vessel in a state in which the foreign substance capturing catheter 20 and the foreign substance removing catheter 30 are set inside the sheath portion 10. Therefore, it is not necessary to use an introducer sheath or dilator. In other words, since it is possible to save time and effort required for drawing out the dilator, the burden on the user is reduced. Furthermore, since the medical device 1 is inserted into the blood vessel while the foreign substance capturing catheter 20 and the foreign substance removing catheter 30 are set inside the sheath portion 10, it is possible to prevent collapsing or kinking of the sheath portion at the time of insertion of the medal device into the body.

When percutaneously inserting a foreign substance removing catheter of the related art into a blood vessel using an introducer sheath, an accessory called an inserter or the like is required to insert the foreign substance removing catheter into the introducer sheath.

In contrast, with the medical device 1 of the first exemplary embodiment, since the foreign substance capturing catheter 20 and the foreign substance removing catheter 30 are preliminarily set inside the sheath portion 10, the use of the inserter is unnecessary. As a result, the number of parts of a whole product is reduced, which results in cost reduction.

Since the medical device 1 has the distal end tip 38 structured as described above, when the medical device 1 is inserted into the blood vessel, the open end 18 of the sheath tube 12 is closed by the distal end tip 38, which prevents blood from entering the sheath tube 12. In addition, the distal end tip 38 can reduce insertion resistance when the medical device 1 is inserted along the guide wire. Further, the distal end tip 38 can unclose the open end 18 by simply moving the foreign substance removing catheter 30 in a distal direction relative to the sheath portion 10. Therefore, the medical device 1 is easy to operate for users.

In the medical device 1, since the sheath portion 10 is provided with the first valve 16, and the foreign substance capturing catheter 20 is provided with the second valve 26, it is possible to prevent the foreign substance from undesirably falling off from the foreign substance capturing catheter 20 or the foreign substance removing catheter 30. Further, for example, when the foreign substance capturing catheter 30 is moved forward or backward within the blood vessel, the first valve 16 and the second valve 26 can prevent the displacement of the foreign substance capturing catheter 20, thereby preventing an undesirable positional deviation of the catheters.

Figure 3:
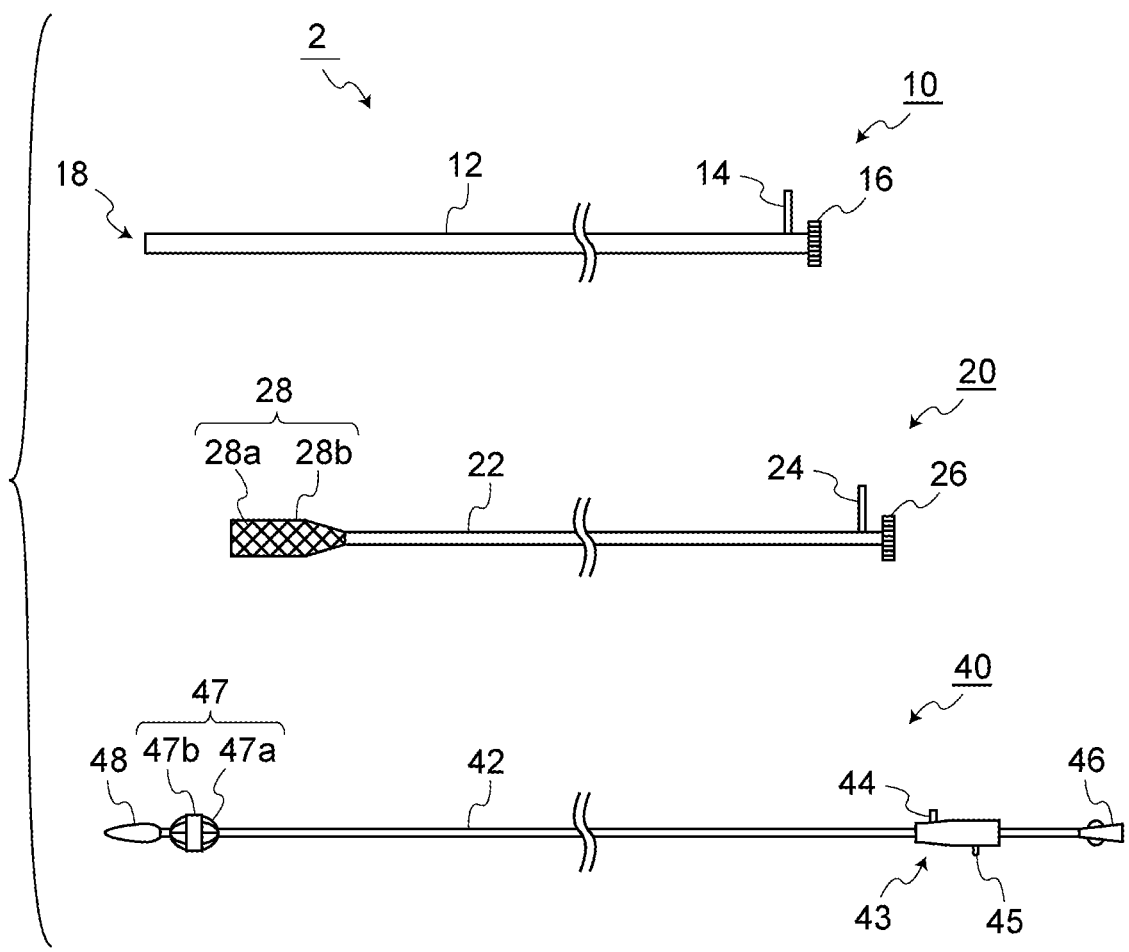
FIG. 3 illustrates an overall configuration of a medical device according to a second exemplary embodiment of the present invention.

FIG. 3 illustrates the overall configuration of the medical device 2 according to a second exemplary embodiment of the invention. Regarding the medical device 2, in FIG. 3, the same elements as those in FIG. 1 are denoted by same reference numerals.

The medical device 2 is configured to stop bleeding from the inner wall of the blood vessel. As illustrated in FIG. 3, the medical device 2 includes a tubular sheath portion 10, a foreign substance capturing catheter 20 configured to be movable through the sheath portion 10, and an intravascular hemostasis catheter 40 configured to be movable though the foreign substance capturing catheter 20.

Since the sheath portion 10 and the foreign substance capturing catheter 20 illustrated in FIG. 3 are the same as those described in the exemplary embodiment of FIG. 1, a description thereof will be omitted.

The intravascular hemostasis catheter 40 serving as a treatment catheter includes an elongated catheter tube 42, an operation portion 43 disposed at a proximal portion of the catheter tube 42, an injection port 44 and an operation level 45 installed on a flank surface of the operation portion 43, a connector 46 provided at a proximal end of the catheter tube 42, a hemostasis portion 47 provided at a distal portion of the catheter tube 42, and a distal end tip 48 provided at a distal end of the catheter tube 42. The intravascular hemostasis catheter 40 is, for example, a catheter used for stopping bleeding from a blood vessel wall.

Since the catheter tube 42, the operation portion 43, the injection port 44, the operation lever 45, the connector 46, and the distal end tip 48 illustrated in FIG. 3 are the same as those described in the exemplary embodiment of FIG. 1, a description thereof will be omitted.

The hemostasis portion 47 includes an elastically deformable portion 47a arranged to plural the metal wires extend along the tube axial direction (the longitudinal direction of the intravascular hemostasis catheter 40), expanding to become a substantially spherical shape, and contracting to become a tubular shape having a diameter substantially the same as the catheter tube 42, and a hemostatic membrane 47b arranged at a middle portion (a maximum diameter when the elastically deformable portion 47a is expanded) of the elastically deformable portion 47a.

As the material of the metal wire constituting the elastically deformable portion 47a, for example, a well-known metal or a metal alloy typified by stainless steel, a Ni—Ti alloy, a titanium alloy or the like may be preferably used. In addition, the metal wires are made from a material having super-elasticity (a reversible property of returning to its original shape from a deformed state as soon as the force is removed). As a material having super-elasticity, for example, a Ni—Ti alloy may be suitably used. Note that when a metal alloy having X-ray contrasting properties is used as the material of the elastic deformable portion, the elastic deformable portion may function as an X-ray impermeable marker. In this case, the position of the removing portion can be identified from the outside of the body.

The hemostatic membrane 47b is a film-like member stretched over the entire circumference of the elastically deformable portion 47a and is made of a flexible material that can conform to the expanded shape and the contracted shape of the elastic deformable portion 47a.

As the material of the hemostatic membrane 47b, for example, materials such as polyurethane, polyethylene, polyester, polypropylene, polyimide, polytetrafluoroethylene (PTFE), polyvinylidene fluoride, and the like can be suitably used.

As described above, the medical device 2 differs from the medical device 1 of FIG. 1 in the type of treatment catheter. However, as in the case of the medical device 1, in a state in which the foreign substance capturing catheter 20 and the intravascular hemostasis catheter 40 are set inside the sheath portion 10, the medical device 2 may be inserted into the blood vessel, so that it is not necessary to use an introducer sheath or dilator. In other words, since it is possible to save time and effort required to extract the dilator, it is possible to reduce the burden on the user. Since the medical device 2 is inserted into the blood vessel in a state in which the foreign substance capturing catheter 20 and the intravascular hemostasis catheter 40 are set inside the sheath portion 10, collapsing and kinking of the sheath portion 10 can be prevented at the time of insertion of the medical device into the body.

Since the medical device 2 has the same construction as the medical device 1 of FIG. 1 except for the type of the treatment catheter, the medical device has the corresponding effects among effects of the medical device 1.

Figure 4:
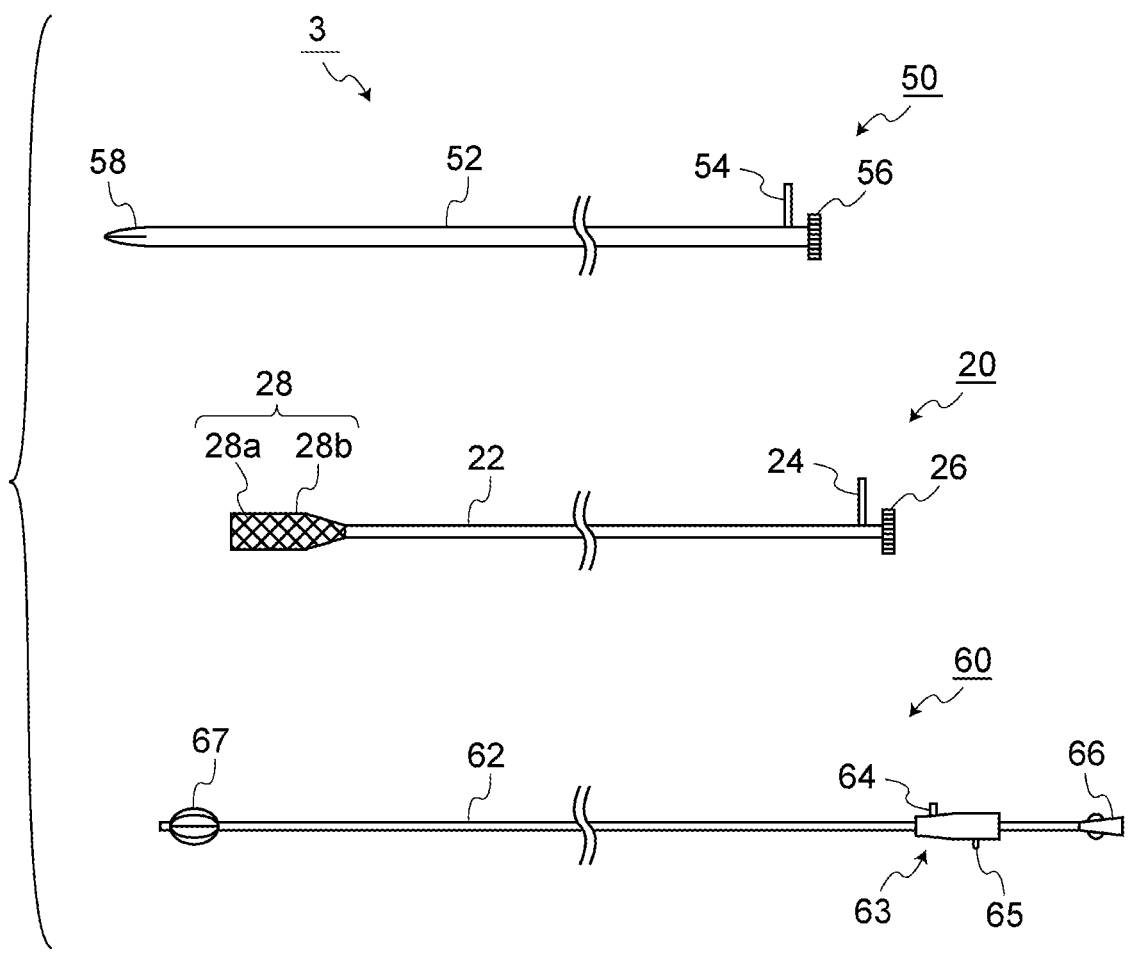
FIG. 4 illustrates an overall configuration of a medical device according to a third exemplary embodiment of the present invention.
Figure 5A:
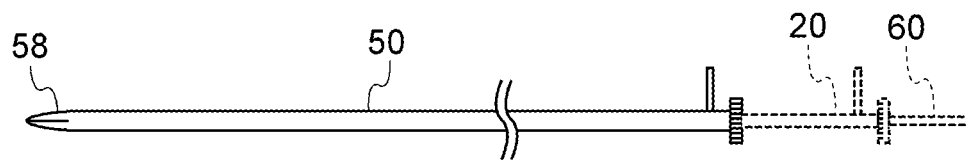
FIG. 5A illustrates a state in which a distal end of a sheath portion of the medical device of FIG. 4 is closed.
Figure 5B:
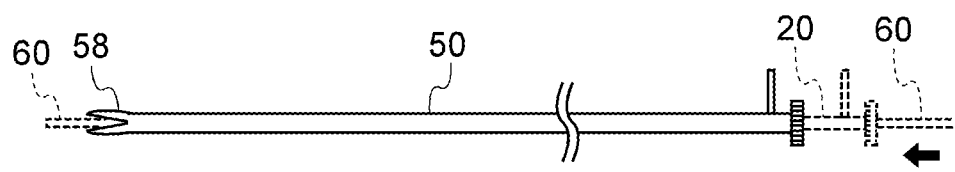
FIG. 5B illustrates a state in which the distal end of the sheath portion of the medical device of FIG. 4 is opened.

FIG. 4 illustrates the overall configuration of a medical device 3 according to a third exemplary embodiment of the present invention. FIG. 5A illustrates a state in which a distal end 58 of a sheath portion 50 of the medical device 3 is closed, and FIG. 5B illustrates a state in which the distal end 58 of the sheath portion 50 of the medical device 3 is open. In FIG. 4, the same components as those shown in FIG. 1 are denoted by the same reference numerals.

The medical device 3 basically has the same construction as the medical device 1 of FIG. 1, but the sheath portion and the foreign substance removing catheter of the medical device 3 differ from those of the medical device 1.

That is, as illustrated in FIGS. 5A and 5B, the sheath portion 50 of the medical device 3 is structured such that the distal end 58 of a sheath tube 52 is deformable. More specifically, for example, the distal end 58 of the sheath tube 52 is provided with a predetermined break line. Before the medical device 3 is used, the medical device 3 is in the state illustrated in FIG. 5A, in which the foreign substance removing catheter 60 is set inside the foreign substance capturing catheter 20, the foreign substance capturing catheter 20 is set inside the sheath portion 50, and the distal end 58 of the sheath portion 50 is closed. In this state, the medical device 3 is inserted into the blood vessel. Afterwards, when the foreign substance capturing catheter 20 and the foreign substance removing catheter 20 are moved forward (moved in a direction of the arrow in FIG. 5B) relative to the sheath portion 50, the distal end 58 of the sheath 50 is cut apart at the break line, whereby the distal end of the sheath portion 50 is unclosed (i.e., opened).

Further, as illustrated in FIG. 4, the distal end tip 38 described in the first exemplary embodiment is not provided at the distal end of the foreign substance removing catheter 60 in the third exemplary embodiment.

Regarding the sheath portion 50 and the foreign substance removing catheter 60 of the medical device 3, the other components have the same construction as those in the first exemplary embodiment of FIG. 1. In addition, since the foreign substance capturing catheter 20 illustrated in FIG. 4 is the same as the catheter explained in the first exemplary embodiment of FIG. 1, a description of those components will be omitted.

As described above, the medical device 3 differs from the medical device 1 of FIG. 1 in terms of the construction of the sheath portion and the foreign substance removing catheter. However, similarly to the case of the medical device 1, in a state in which the foreign substance capturing catheter 20 and the foreign substance removing catheter 60 are set inside the sheath portion 50, the medical device 3 can be inserted into a blood vessel. Therefore, it is not necessary to use an introducer sheath or dilator for the medical device 3. In other words, since it is possible to save time and effort required to extract the dilator, it is possible to reduce the burden on the user. Since the medical device 3 is inserted into the blood vessel in a state in which the foreign substance capturing catheter 20 and the foreign substance removing catheter 60 are set inside the sheath portion 50, collapsing and kinking of the sheath portion can be suppressed when the medical device 3 is inserted.

Since the medical device 3 has the same construction as the medical device 1 of FIG. 1 except for the construction of the sheath portion and the foreign substance removing catheter, the medical device 3 has the corresponding effects among the effects of the medical device 1.

While the present invention has been described with reference to certain exemplary embodiments thereof, it will be understood by those skilled in the art that various changes and modifications may be made therein. For example, the following modifications are possible.

The first anti-falling structure (the first valve) may not be provided on the sheath portion, and instead, may be provided on the foreign substance capturing catheter. In another example, the first anti-falling structure may provided on both the sheath portion and the foreign substance capturing catheter.

The second anti-falling structure (the second valve) may not be provided on the foreign substance capturing catheter, and instead, may be provided on the treatment catheter (the foreign substance removing catheter or the intravascular hemostasis catheter). In another example, the second anti-falling structure may be provided on both the foreign substance capturing catheter and the treatment catheter.

In a state in which the foreign substance capturing catheter and the foreign substance removing catheter (or the intravascular hemostasis catheter) are set inside the sheath portion, as illustrated in FIG. 2, although the case where the capturing portion of the foreign substance capturing catheter is arranged at a more distal side than the removing portion of the foreign substance removing catheter (or the hemostasis portion of the intravascular hemostasis catheter) has been described, the invention is not limited thereto. For example, the following construction is possible: the capturing portion of the foreign substance capturing catheter is arranged at a more proximal side than the removing portion of the foreign substance removing catheter (or the hemostasis portion of the intravascular hemostasis catheter). Alternatively, the following construction is also possible: the removing portion of the foreign substance removing catheter (or the hemostasis portion of the intravascular hemostasis catheter) and the capturing portion of the foreign substance capturing catheter are arranged at almost the same position. For example, the removing portion in a collapsed state may be accommodated in the capturing portion The expanded shape of the removing portion and the elastically deformable portion is not limited to prolate, and may be, for example, spherical, oblate, or egg shaped. In another example, respective end portions of the removing portion or the elastically deformable portion may have prolate shape and an intermediate portion of the retriever may be cylindrical cylindrical.

The removing portion and the elastically deformable portion may not be made of a metallic material. For example, a biocompatible resin or the like may be used for the removing portion and the elastically deformable portion.

The membrane portion may not cover the entire mesh portion of the capturing portion. For example, a tapered portion of the mesh portion (a proximal portion of the mesh portion) may be exposed without being covered by the membrane portion. The material of the mesh portion is not limited to metal, and may be a biocompatible resin or the like.

The treatment catheter may not be configured as a foreign substance removing catheter or an intravascular hemostasis catheter. For example, the present invention is applicable with other types of treatment catheter such as a foreign substance dissolving catheter configured to dissolving foreign substance.

The present invention is not limited to a medical device for treating a blood vessel. The present invention is applicable to a medical device for removing foreign substance in other tubular tissues such as a gastrointestinal tract and a bile duct.

What is claimed is:

1. A medical device configured to treat a body cavity, the medical device comprising:
   a sheath portion having a tubular shape;
   a foreign substance capturing catheter configured to be movable inside the sheath portion, and comprising a capturing portion configured to capture a foreign substance inside the body cavity; and
   a treatment catheter configured to be movable inside the foreign substance capturing catheter, and comprising:
      a treatment portion configured to treat the body cavity, the treatment portion comprising a plurality of metal wires and being configured to expand and contract, and
      a distal end tip disposed at a distal end portion of the treatment catheter and configured to prevent blood from entering the sheath portion from the body cavity,
   wherein the medical device is configured to be inserted into the body cavity in a state in which the treatment catheter is set inside the foreign substance capturing catheter and the foreign substance capturing catheter is set inside the sheath portion,
   wherein the treatment portion and the distal end tip are separated from each other by a distance along the treatment catheter,
   wherein a first valve is provided at a proximal end portion of the sheath portion and is configured to prevent the foreign substance capturing catheter from falling off from the sheath portion and to prevent blood from leaking from the sheath portion, and
   wherein a second valve is provided at a proximal end portion of the foreign substance capturing catheter, and is configured to prevent a displacement of the treatment catheter and to prevent blood from leaking from the foreign substance capturing catheter.

2. The medical device according to claim 1,
   wherein the distal end tip of the treatment catheter is configured to close an open end of the sheath portion in a state in which the treatment catheter is set inside the foreign substance capturing catheter and the foreign substance capturing catheter is set inside the sheath portion, and
   wherein the distal end tip of the treatment catheter is configured to unclose the open end of the sheath portion with a movement of the treatment catheter in a distal direction relative to the sheath portion.

3. The medical device according to claim 1, wherein a distal end of the sheath portion is configured to be closed in a state in which the treatment catheter is set inside the foreign substance capturing catheter and the foreign substance capturing catheter is set inside the sheath portion, and
   wherein the distal end of the sheath portion is configured be unclosed with a movement of one of the foreign substance capturing catheter and the treatment catheter in a distal direction relative to the sheath portion.

4. The medical device according to claim 1, wherein the treatment catheter is configured to remove the foreign substance inside the body cavity.

5. The medical device according to claim 1, wherein the treatment catheter is configured to dissolve the foreign substance inside the body cavity.

6. The medical device according to claim 1, wherein the treatment catheter is further configured to stop bleeding from a blood vessel wall.

7. The medical device according to claim 1, wherein the treatment portion is disposed between the distal end tip and the capturing portion.

* * * * *